United States Patent
Andle et al.

[11] Patent Number: 6,033,852
[45] Date of Patent: Mar. 7, 2000

[54] MONOLITHIC PIEZOELECTRIC SENSOR (MPS) FOR SENSING CHEMICAL, BIOCHEMICAL AND PHYSICAL MEASURANDS

[75] Inventors: Jeffrey C. Andle, Bangor; Ryszard M. Lec, Orono, both of Me.

[73] Assignee: University of Maine, Orono, Me.

[21] Appl. No.: 08/938,115

[22] Filed: Sep. 26, 1997

Related U.S. Application Data

[60] Provisional application No. 60/026,795, Sep. 27, 1996.

[51] Int. Cl.⁷ .................................................. G01N 33/543
[52] U.S. Cl. .......................... 435/6; 310/311; 310/313 R; 310/312; 310/340; 310/348; 422/82.01; 435/7.21; 435/7.32; 435/287.1; 435/287.2; 436/518; 436/524; 436/525; 436/527
[58] Field of Search ............................... 310/311, 313 R, 310/312, 340, 348; 422/82.01; 435/6, 7.21, 7.32, 287.1, 287.2; 436/518, 524, 525, 527

[56] References Cited

U.S. PATENT DOCUMENTS

| | | | |
|---|---|---|---|
| 4,236,893 | 12/1980 | Rice | 310/312 |
| 4,242,096 | 12/1980 | Oliveira et al. | 310/312 |
| 4,735,906 | 4/1988 | Bastiaans | 436/806 |
| 4,789,804 | 12/1988 | Karube et al. | 310/311 |
| 4,847,193 | 7/1989 | Richards et al. | 435/6 |
| 4,905,701 | 3/1990 | Cornelius | 435/806 |
| 4,920,296 | 4/1990 | Takahashi et al. | 310/348 |
| 4,999,284 | 3/1991 | Ward et al. | 435/6 |
| 5,001,053 | 3/1991 | Takahashi et al. | 435/4 |
| 5,828,159 | 10/1998 | Miyagawa et al. | 310/340 |

*Primary Examiner*—Christopher L. Chin
*Attorney, Agent, or Firm*—Michael J. Persson; William B. Ritchie

[57] ABSTRACT

A piezoelectric sensor and assembly for measuring chemical, biochemical and physical measurands is disclosed. The piezoelectric sensor comprises a piezoelectric material, preferably a crystal, a common metal layer attached to the top surface of the piezoelectric crystal, and a pair of independent resonators placed in close proximity on the piezoelectric crystal such that an efficacious portion of acoustic energy couples between the resonators. The first independent resonator serves as an input port through which an input signal is converted into mechanical energy within the sensor and the second independent resonator serves an output port through which a filtered replica of the input signal is detected as an electrical signal. Both a time delay and an attenuation at a given frequency between the input signal and the filtered replica may be measured as a sensor output. The sensor may be integrated into an assembly with a series feedback oscillator and a radio frequency amplifier to process the desired sensor output. In the preferred embodiment of the invention, a selective film is disposed upon the grounded metal layer of the sensor and the resonators are encapsulated to isolate them from the measuring environment. In an alternative embodiment of the invention, more than two resonators are used in order to increase the resolution of the sensor.

21 Claims, 2 Drawing Sheets

(AMENDED)

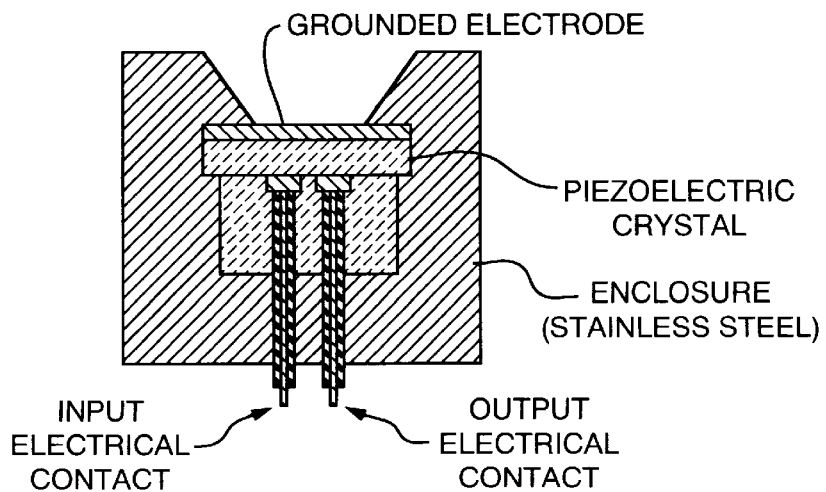
FIG. 2
(AMENDED)

MONOLITHIC PIEZOELECTRIC SENSOR (MPS) FOR SENSING CHEMICAL, BIOCHEMICAL AND PHYSICAL MEASURANDS

This application claims benefit of provisional 60/026,795 Sep. 27, 1996.

STATEMENT OF GOVERNMENT INTEREST

The United States Government has rights in this invention pursuant to Contract No. DE-FG02-97PC82335 awarded by the United States Department of Energy, and Contract No. DAMD17-95C-5033 awarded by the United States Army.

BACKGROUND OF THE INVENTION

1. Field of the Invention

The invention relates to sensing chemical, biochemical and physical measurands using piezoelectric sensors.

2. Description of the Related Art

There are a number of sensor applications that demand exceptional physically, chemically and environmentally stable sensing elements. Two classes of sensors which are frequently proposed to this end are the optical fiber based sensors and the piezoelectric sensors, both of which derive their chemical and physical stability from solid state construction of inert glassy or crystalline solids. One advantage of the piezoelectric sensors is their wide range of potential sensing mechanisms coupled with the exceptional temperature stability of the most common implementation, namely quartz crystal technology.

Various piezoelectric sensor geometries have been proposed and patented. The most widely considered of these is the quartz crystal microbalance, though other piezoelectric crystals, polymers and composites have also been used. Though the original patents in this field are expired, the technology is still not a mature technique for many sensing applications.

U.S. Pat. No. 4,760,351, issued to Newell et al., teaches the use of arrays of these devices which consist of a parallel plate capacitor employing a piezoelectric material as the dielectric support. While this structure has exhibited good sensing characteristics in the vapor phase, sensor performance is substantially impaired when fluid phase operation is pursued.

U.S. Pat. No. 5,374,521, issued to Kipling et al., discloses an alternative mode of operation of these sensors intended to overcome these difficulties; however, the method is not amenable to field deployment or mass production.

The preferred methods of operating the crystal sensor are (1) using an impedance analyzer in a laboratory setting or (2) incorporating the device into an oscillating circuit. Under vapor phase operation, both techniques are suitable; however, liquid phase operation incurs many difficulties in instrumentation, which substantially impair the reliability and sensitivity of the sensor.

U.S. Pat. No. 4,847,193, issued to Richards et al., discloses a signal amplification technique which partially overcomes this problem in selected assays. U.S. Pat. No. 5,179,028, issued to Vali et al. discloses an alternative structure which replaces the parallel plate capacitor with a tuning fork geometry. This geometry appears to offer other measurement methods but does not overcome the difficulties associated with liquid phase operation.

U.S. Pat. No. 4,735,906, issued to Bastiaans, discloses a surface wave device which supports two separate interdigital transducers which serve to convert energy between electrical and acoustic signals. These transducers employ arrays of electrodes which are periodically spaced on the surface of the crystal and are alternately connected to the positive and negative terminals of the electrical input or output.

U.S. Pat. No. 5,306,644, issued to Myerholtz et al. teaches an improvement on Bastiaans invention by employing a specific combination of materials and structural design to substantially reduce mechanical interactions with the fluid medium. Myerholtz et al. also discloses the expansion of a single sensor to an array.

U.S. Pat. No. 5,478,756, issued to Gizeli et al. teaches an alternative improvement on the Bastiaans structure which employs a thick film of dielectric material to help confine the acoustic signal to the surface.

All these approaches suffer from two significant limitations. The foremost of these is that the structures do not isolate the electrical connections from the sensing environment. One solution has been to employ an acoustic waveguide version of the Bastiaans structure. While this structure overcomes the most substantial limitations of the Bastiaans structure, it incurs additional spurious resonances which further complicate the sensor instrumentation. Finally, all of the Bastiaans-derived structures require micron scale lithography and teach towards complicated, surface-based devices. A simpler implementation is based upon the (quartz) crystal microbalance devices. The fundamental problem with these techniques, however, is that the sensing element is a simple reactive electrical component with a single electrical "port".

There is not found in the prior art a sensing apparatus which has no additional spurious resonances, separate input and output terminals, and isolates the electrical connections to the circuit from the sensing environment.

SUMMARY OF THE INVENTION

It is an aspect of the invention to provide a sensing apparatus which has separate input and output terminals.

It is another aspect of the invention to provide a sensing apparatus which isolates the electrical connections to the circuit from the sensing environment.

The invention is an improvement on the (quartz) crystal resonator which employs the parallel plate configuration while isolating the non-grounded electrical connections from the sensing medium and providing separate input and output electrical ports. Its relationship to the existing resonator is analogous to the relationship of the transistor to a diode.

Other aspects and advantages of the present invention will become apparent and obvious from a study of the following description and the accompanying drawings which are merely illustrative of the invention.

BRIEF DESCRIPTION OF THE DRAWINGS

FIG. 2 illustrates the monolithic piezoelectric sensor in accordance with the invention.

DETAILED DESCRIPTION OF THE INVENTION

The sensor is a novel piezoelectric apparatus that is useful for sensing chemical, biochemical and physical measurands. The sensor operates by measurement of the perturbations of the electrical parameters of a piezoelectric sensing element. The sensing element is capable of detecting both electrical (e.g. conductivity and permittivity) and mechanical (e.g. elasticity, viscosity and density) perturbations caused by a measurand. The sensing element consists of two or more acoustically coupled resonant structures on a single piezoelectric substrate or a substrate coated with a piezoelectric layer. The resulting structure, known as a monolithic filter, provides separate input and output electrical connections which are physically separated from the common ground electrode, allowing it to be incorporated into a large number of diverse measurement systems. The sensor is attractive for sensing a variety of physical, chemical and biochemical measurands, in particular for trace chemical analysis, including trace vapors, metals and biochemicals—either in solution or in gaseous mixtures—and physical measurands such as acceleration, pressure, etc.

The invention combines the best aspects of (quartz) crystal resonator and other piezoelectric sensor techniques and is a fundamental improvement to the well known quartz crystal microbalance (QCM). While the invention has some of the physical traits of the well known QCM, it also overcomes many limitations of the QCM, especially with respect to fluid phase sensing and sensing in highly corrosive environments.

Figure 1A:
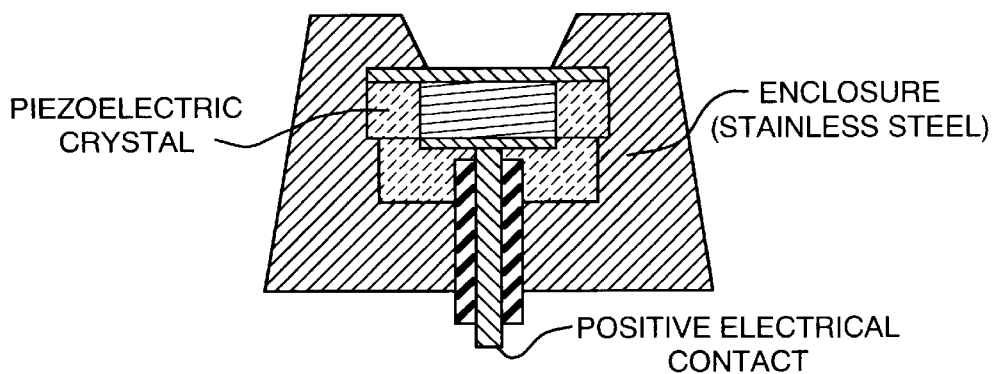
FIG. 1A illustrates a typical prior art piezoelectric sensor.

FIG. 1A illustrates the structure of the traditional QCM device, as it would be employed for fluid-loaded or corrosive environment operation. The only relevant design parameters are the electrode shape, area and the plate thickness. The substrate material is almost always AT-cut quartz, which is chosen for its excellent temperature stability. As shown, the traditional crystal sensor consists of a piezoelectric crystal with metal electrodes on both surfaces. The region between the electrodes supports a mechanical standing wave (denoted by the parallel lines). Electrical connections are made to the grounded side through the case and to the positive side via a wire point contact.

Figure 1B:
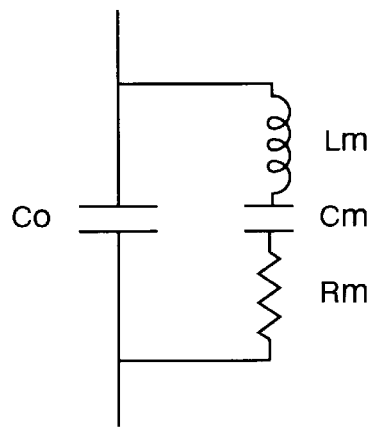
FIG. 1B is a schematic representation of the sensor illustrated in FIG. 1A.

FIG. 1B is a schematic of the equivalent electrical circuit, which consists of a series resonant circuit in parallel with a capacitance. For most frequencies the device appears to be a capacitor, except in a narrow band of frequencies near the resonant frequency of the series branch of the circuit.

The resonant frequency of the crystal is determined by the ratio of the mass (embodied in the equivalent circuit as the inductance) to the stiffness (embodied in the equivalent circuit as the capacitance) and the thickness of the plate. Added mass—which becomes bound to the face of the crystal—increases the inductive component and thus lowers the resonant frequency in a predictable and measurable fashion. It is possible to quantitatively detect nanogram per $mm^2$ and lower levels of mass loading using this technology. The piezoelectric sensor is, itself, a nonspecific mass detector; however, excellent specificity is added by coating the crystal with a selective film, e.g., biochemical receptor film, such as monoclonal antibody, DNA oligonucleotide probes or other suitable bioreceptors or polymer or metallic films. Residual nonspecific binding may be compensated by employing a second, reference crystal which is coated with a different film having similar electrical (charge vs. pH) and mechanical properties. Typically, a second selective receptor is selected which is insignificant to the detection process at hand. Thus, specific tracts of bacterial DNA might be detected using a specific sequence on the sensor crystal while employing a nonsense sequence on the reference sensor.

The most common and cost-effective method of monitoring the resonant frequency employs the crystal as the stabilizing element in an oscillator circuit. The circuit depends on the unique characteristics of the crystal at its resonant frequency. In signal processing and frequency control applications the preferred oscillator circuit places the crystal as a shunt feedback element (between the input and output terminals of an amplifier) and oscillates on the series resonance. This arrangement places both electrodes of the QCM at an active electrical potential and incurs deleterious effects from packaging methods such as that depicted in FIG. 1. To eliminate these effects one of the electrodes must be connected to ground. While this is not inherently a problem, it severely limits the classes of oscillator circuits which may be employed to measure the resonant frequency. In fact, all of the well-known circuits which may be employed with the QCM having one electrode grounded operate as image impedance oscillators. These circuits employ a transistor or other active device in an unstable mode of operation and employ the crystal to control the instability. For example, an inductive component between a transistor's base and ground will induce instability. This class of circuits typically requires that the net electrical characteristics are inductive at the frequency of oscillation. This is difficult to ensure under fluid loading, in which case the resonant branch of the circuit is highly damped and the parallel capacitor dominates. Other instability-based oscillators employ a capacitive element between a transistor's emitter and ground. While the crystal can serve this role, it is capacitive at virtually all frequencies and is thus not a reliable method of stabilizing an oscillator.

As previously stated, oscillator circuits which employ the QCM as a shunt feedback element have excellent stability characteristics. Typically, these circuits employ unconditionally stable amplifiers which provide adequate gain to overcome the resistive losses in the QCM. When the electrical phase shift around the loop is a multiple of $2\pi$ radians, signals are successively amplified on each transit around the loop until the transistor saturates. Since noise signals are capable of starting this process, such a circuit invariably oscillates. Unfortunately, all of the circuits which employ this mode of operation require that two separate electrodes be electrically active with respect to ground. This has proven extremely problematic when using the packaging proposed in FIG. 1 or any suitable alternative. The fundamental constraint is that the QCM is a two-terminal device and one of the terminals must be placed in contact with the fluid. This fluid-loaded electrode must be grounded for reliable electrical operation.

FIG. 2 illustrates the monolithic piezoelectric sensor (MPS) invention, which is based on the (quartz) multi-resonator monolithic filter technology. The MPS employs two driven electrodes referenced to a grounded metal layer (top). The grounded metal layer (typically gold) may be coated with covalently attached bioreceptors (e.g. antibody, enzyme or DNA), or with any other materials that selectively bind their analyte. The added mass changes the frequency response in a predictable and measurable fashion. This shift is typically monitored by embedding the sensor in a series feedback oscillator. The three-terminal MPS may be employed in series feedback oscillators while still allowing sensing to occur on a grounded, physically-isolated electrode. The invention comprises two or more independent resonators placed in close proximity on the same crystal, such that some acoustic energy couples between them.

Figure 3:
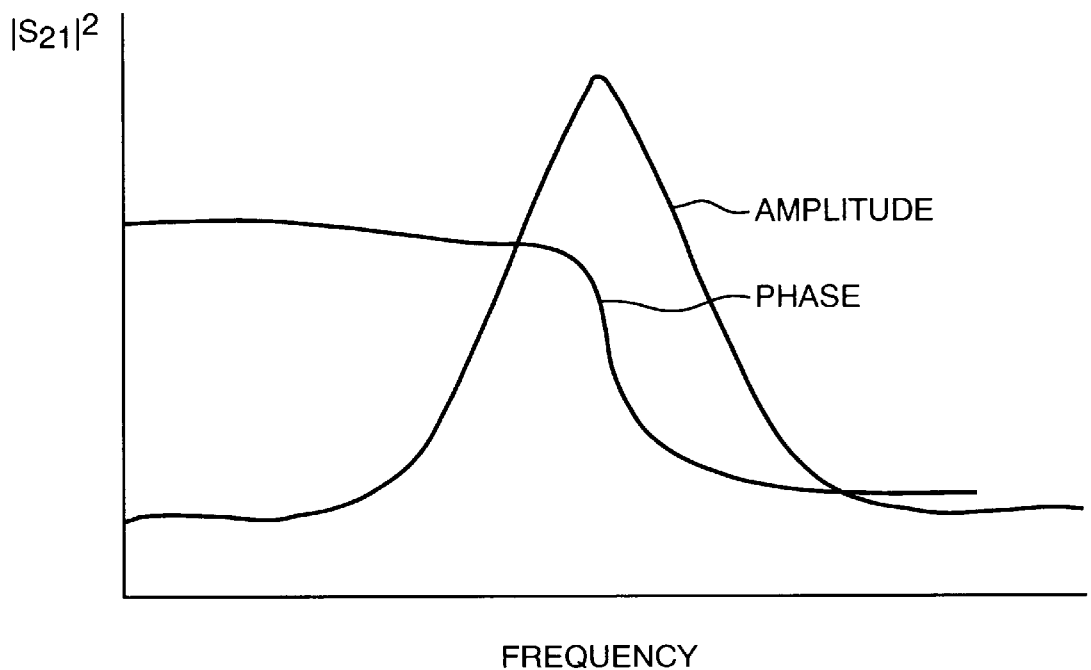
FIG. 3 is a graph showing electrical transmission and phase as a function of frequency of the sensor shown in FIG. 2.

The net result is a sharp, well defined filter function, as shown in FIG. 3. Electrical transmission and phase is plotted as a function of frequency. When placed in the feedback path of an amplifier, the resulting circuit can be induced to oscillate at a fixed frequency for which there is net gain around the loop and the phase shift is a multiple of 360 degrees. Extremely stable oscillation occurs when the frequency is designed to be in the center of the resonance, in the area of high phase slope. Since the entire response shifts with mass loading, stable operation is maintained over all cases of sensor operation.

The electrical signal applied to the input appears at the output with a finite attenuation and a well-defined phase shift. By placing the device in the feedback path of a radio-frequency (RF) amplifier, the stable resonance of the crystal controls the frequency of oscillation in the circuit.

The only substantial effects of loading the crystal with a viscous fluid are to slightly increase the attenuation and to lower the oscillation frequency proportional to the viscoelastic properties of the liquid and the added mass due to accumulation of the target chemical in accordance with well-known mathematical models. It is known that during surface reactions, detectable levels of mass change occur on the face of the crystal. Therefore, by measuring the frequency change and the attenuation change of the oscillator, one can quantitate surface reactions and . . . using calibration data . . . determine solution titer.

Figure 4:
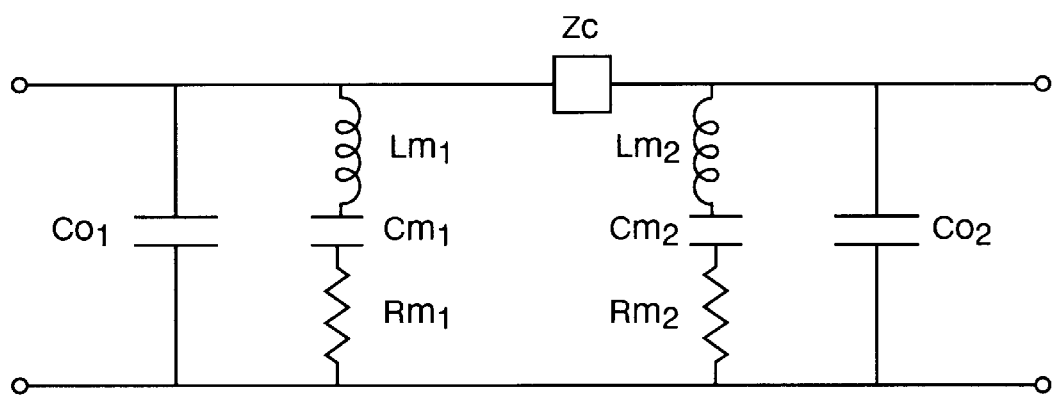
FIG. 4 is a schematic representation of the MPS shown in FIG. 2.

In the case of loading the MPS with conductive materials, such as conductive liquids or thin solid films, the coupling impedance, Zc of FIG. 4, undergoes changes due to the changes of both the dielectric constant and the conductivity of a loading material. Several chemical, biochemical and physical processes change the electric properties of materials. Examples include sensing gas by thin metal oxide films or quantitating metal ions in water. As a result, the resonant frequency and the amplitude of the MPS vary accordingly allowing for determination of the acting measurands.

A MPS sensor offers a very attractive apparatus for sensing a variety of physical measurands such as pressure, acceleration, electric field, temperature, etc. In this case, the measurand of interest directly changes the MPS substrate parameters such as elastic, dielectric or piezoelectric constants. As a result, the frequency and amplitude of the MPS changes accordingly. For example, the pressure or electric field applied to the MPS changes the elastic constants of the substrate via nonlinear elasto-acoustic and electro-acoustic effects.

In its simplest form, the sensor comprises a piezoelectric plate with at least two resonators placed in proximity, as shown in FIG. 2. Each resonator comprises two electrodes—placed on opposite surfaces for in-line excitation, as shown, or on the same surface for parallel excitation (not shown). The electrodes consist of a conductor, such as gold, silver or aluminum. The selection of the electrode metal is determined by the environmental issues associated with the specific application and with the frequency of operation. Very high frequency devices tend to employ aluminum for its superior mechanical properties. Lower frequency devices typically prefer silver or gold for environmental stability (corrosion resistance). The design rules for electrode thickness are determined by energy trapping theory, as is the spacing between the adjacent resonators. A variety of electrode shapes are possible. Traditionally, rectangular electrodes are employed in analogous signal processing devices for mathematical simplicity; however, elliptical and circular electrodes are also known in these applications. Sensor elements are feasible with any possible electrode geometries, including elliptical, rectangular, toroidal, etc.

In this configuration, one resonator serves as an input port through which electrical energy is converted to mechanical energy within the sensor. The second resonator serves as an output port, through which a filtered (delayed and attenuated) replica of the input signal is detected as an electrical signal. Both the delay time and the attenuation at a given frequency may be affected by the measurand and may be measured as the sensor output.

The structure of FIG. 3 would be sensitive to physical (e.g. acceleration, pressure), electrical (e.g. conductivity, etc.) and mechanical (e.g. mass loading or viscoelastic loading) perturbations. Selective films may be employed on either surface of the sensor or on both surfaces simultaneously, allowing three configurations of the sensor. The sensor may be packaged so as to expose either or both surfaces to the test environment. Although any of these configurations is acceptable, the preferred approach is to place the film on the grounded surface and enclose the electrical connections (input and output electrodes) in isolation.

In some cases, it would be preferable to eliminate electrical perturbations, for example, in a mass-based sensor. This may be accomplished by employing a continuous ground electrode, as shown in FIG. 2, and encapsulating the active input and output electrodes. Since the electric field is shorted everywhere on the sensing surface, spurious changes in the conductivity of the test solution would not cause deleterious sensor drift.

Finally, in some applications and/or instrumentation methods it may be desirable to employ a multi-pole filter consisting of more than two resonators in proximity. The primary advantage of this approach is to increase the phase slope versus frequency, allowing better resolution. The ability to resolve phase changes increases approximately linearly with the number of resonators.

It is feasible to place different films over the different resonators and to employ spectroscopic measurements and neural network techniques to deconvolve the individual perturbations.

While there have been described what are at present considered to be the preferred embodiments of this invention, it will be obvious to those skilled in the art that various changes and modifications may be made therein without departing from the invention and it is, therefore, aimed to cover all such changes and modifications as fall within the true spirit and scope of the invention.

What is claimed is:

1. A piezoelectric sensor comprising:

a piezoelectric crystal having a top surface and a bottom surface;

a common metal layer attached to said top surface of said piezoelectric crystal; and a first independent resonator and a second independent resonator placed in close proximity on said bottom surface of said piezoelectric crystal, such that an efficacious portion of acoustic energy couples between said resonators;

wherein said first independent resonator and said second independent resonator each comprise at least two conductive electrodes, wherein said first independent resonator serves as an input port trough which an input signal is converted into medical energy within said sensor, and wherein said second independent resonator serves an output port trough which a filtered replica of said input signal is detected as an electrical signal.

2. The sensor as claimed in claim 1 further comprising a selective film disposed upon at least a portion of one of said surfaces of said piezoelectric crystal.

3. The sensor as claimed in claim 2 wherein said selective film is disposed upon said common metal layer.

4. The sensor assembly as claimed in claim 3 wherein said selective film is an electrochemically active film.

5. The sensor as claimed in claim 4 wherein said selective film selectively binds chemicals chosen from group consisting of pathogens, genomic biochemicals and immunochemicals.

6. The sensor assembly as claimed in claim 3 wherein said selective film selectively binds chemicals via solvent-solute interactions.

7. The sensor as claimed in claim 1 wherein said sensor output corresponds to a variable in a process chosen from a group consisting of chemical processes, biochemical processes and physical processes.

8. The sensor as claimed in claim 1 wherein said resonators are encapsulated such that said resonators are electrically isolated from said common metal layer.

9. The sensor as claimed in claim 8 wherein said common metal layer is continuously connected such that an electric field formed about said common metal layer is shorted.

10. The sensor as claimed in claim 8 wherein said common metal layer is split such that electric fields generated by said resonators interact with a sensing environment.

11. A piezoelectric sensor assembly comprising:
   a series feedback oscillator;
   a radio-frequency amplifier; and
   a piezoelectric sensor comprising;
      a piezoelectric crystal having a top surface and a bottom surface;
      a common metal layer attached to said top surface of said piezoelectric crystal; and
      a first independent resonator and a second independent resonator placed in close proximity on said bottom surface of said piezoelectric crystal, such that an efficacious portion of acoustic energy couples between said resonators;
      wherein said first independent resonator and said second independent resonator each comprise at least two conductive electrodes, wherein said first independent resonator serves as an input port through which an input signal is converted into mechanical energy within said sensor, and wherein said second independent resonator serves an output port through which a filtered replica of said input signal is detected as an electrical signal; and
   wherein said piezoelectric sensor is placed in a feedback path of said amplifier to form a loop and is induced by said series feedback oscillator to oscillate at a frequency for which there is a net gain around said loop and such that a phase shift of a multiple of 360 degrees occurs.

12. The sensor assembly as claimed in claim 11 wherein said sensor further comprises a selective film disposed upon at least a portion of one of said surfaces of said piezoelectric crystal.

13. The sensor assembly as claimed in claim 12 wherein said selective film is disposed upon said common metal layer.

14. The sensor assembly as claimed in claim 13 wherein said selective film is an electrochemically active film.

15. The sensor assembly as claimed in claim 14 wherein said selective film selectively binds chemicals chosen from group consisting of pathogens, genomic biochemicals and immunochemicals.

16. The sensor assembly as claimed in claim 13 wherein said selective film selectively binds chemicals via solvent-solute interactions.

17. The sensor assembly as claimed in claim 11 wherein said sensor output corresponds to a variable in a process chosen from a group consisting of chemical processes, biochemical processes and physical processes.

18. The sensor assembly as claimed in claim 11 wherein said resonators are encapsulated such that said resonators are electrically isolated from said common metal layer.

19. The sensor assembly as claimed in claim 11 wherein said common metal layer is continuously grounded such that an electric field formed about said grounded metal layer is shorted.

20. The sensor assembly as claimed in claim 11 wherein said common metal layer is split such that electric fields generated by said resonators interact with a sensing environment.

21. The sensor assembly as claimed in claim 11 wherein an amplifier phase is switched between at least two different values such that at least two different frequencies are measured by said sensor.

* * * * *

UNITED STATES PATENT AND TRADEMARK OFFICE
CERTIFICATE OF CORRECTION

PATENT NO. : 6,033,852  Page 1 of 1
APPLICATION NO. : 08/938115
DATED : March 7, 2000
INVENTOR(S) : Jeffrey C. Andle and Ryszard M. Lec It is certified that error appears in the above-identified patent and that said Letters Patent is hereby corrected as shown below:

Title page - item (57) Abstract, Line 11 - -- as -- should be inserted between "serves an"

Column 4, line 1 - "tracts" should be -- traits --

Column 6, line 13 - "FIG. 3" should be -- FIG. 2 --

Column 6, line 67 - "trough" should be -- through --

Column 7, line 1 - "medical" should be -- mechanical --

Column 7, line 3 - "trough" should be -- through --

Column 7, line 10 - remove the word "assembly"

Column 7, line 16 - remove the word "assembly"

Column 7, line 19 - "said" should be -- a --

Column 8, line 3 - -- as -- should be inserted between "serves an"

Signed and Sealed this

Twenty-fifth Day of March, 2008

JON W. DUDAS
*Director of the United States Patent and Trademark Office*